US008569053B2

(12) United States Patent
Seidel et al.

(10) Patent No.: US 8,569,053 B2
(45) Date of Patent: *Oct. 29, 2013

(54) IN-VITRO FERTILIZATION SYSTEMS WITH SPERMATOZOA SEPARATED INTO X-CHROMOSOME AND Y-CHROMOSOME BEARING POPULATIONS

(75) Inventors: George E. Seidel, Laporte, CO (US); Kehuan Lu, Nanning (CN); Tae Kwang Suh, Fort Collins, CO (US)

(73) Assignee: XY, LLC, Navasota, TX (US)

( * ) Notice: Subject to any disclaimer, the term of this patent is extended or adjusted under 35 U.S.C. 154(b) by 46 days.

This patent is subject to a terminal disclaimer.

(21) Appl. No.: 13/404,706

(22) Filed: Feb. 24, 2012

(65) Prior Publication Data

US 2012/0164733 A1    Jun. 28, 2012

Related U.S. Application Data

(63) Continuation of application No. 11/508,133, filed on Aug. 21, 2006, now Pat. No. 8,137,967, which is a continuation of application No. 10/433,191, filed as application No. PCT/US01/45237 on Nov. 29, 2001, now Pat. No. 7,094,527.

(60) Provisional application No. 60/253,785, filed on Nov. 29, 2000, provisional application No. 60/253,787, filed on Nov. 29, 2000.

(51) Int. Cl.
*C12N 5/02* (2006.01)

(52) U.S. Cl.
USPC .......................... 435/325; 435/373; 435/363

(58) Field of Classification Search
CPC ........................ A61K 35/14; A61K 2035/124
USPC ..................................... 435/2, 325, 373, 363
See application file for complete search history.

(56) References Cited

U.S. PATENT DOCUMENTS

| 5,021,244 | A | * | 6/1991 | Spaulding | 530/388.2 |
|---|---|---|---|---|---|
| 5,084,004 | A | * | 1/1992 | Ranoux | 600/34 |
| 5,135,759 | A | | 8/1992 | Johnson | |
| 5,514,537 | A | | 5/1996 | Chandler | |
| 5,563,059 | A | * | 10/1996 | Alak et al. | 800/21 |
| 6,153,373 | A | * | 11/2000 | Benjamin et al. | 435/2 |
| 7,094,527 | B2 | | 8/2006 | Seidel et al. | |
| 8,137,967 | B2 | * | 3/2012 | Seidel et al. | 435/373 |

FOREIGN PATENT DOCUMENTS

WO    WO 99/33956    7/1999

OTHER PUBLICATIONS

Menezo et al. Fertility and Sterility, vol. 42, No. 5, Nov. 1984, p. 750-755.*
U.S. Appl. No. 11/508,133, filed Aug. 21, 2006.
U.S. Appl. No. 10/433,191, filed May 29, 2003, now United States Patent No. 7,094,527, issued Aug. 22, 2006.
International Patent Cooperation Treaty Patent Application No. PCT/US01/45237, filed Nov. 29, 2001.
U.S. Appl. No. 60/253,785, filed Nov. 29, 2000.
U.S. Appl. No. 60/253,787, filed Nov. 29, 2000.
Lu, et al. In Vitro Fertilization with Flow-Cytometrically-Sorted Bovine Sperm, Theriogenology 1999, 52-8, pp. 1393-1405.
Olson, et al. Reduced Oxygen Tension and EDTA Improve Bovine Zygote Development in a Chemically Defined Medium, J. Anim. Sci. 2000, 78, pp. 152-157.
Tervit, et al. Successful Culture in Vitro of Sheep and Cattle Ova, J. Reprod. Fert. 1972, 30, pp. 493-497.
Corresponding Canadian patent application No. 2,468,774, OA mailed Mar. 7, 2011, 3 total pages.
Corresponding Canadian patent application No. 2,468,774, OA mailed Mar. 13, 2012, 3 total pages.
Corresponding Canadian patent application No. 2,468,774, OA mailed Jan. 4, 2013, 2 total pages.
Fugger et al. Births of normal daughters after MicroSort sperm separation and intrauterine insemination, in-vitro fertilization, or intracytoplasmic sperm injection. Human Reproduction, Sep. 1998, vol. 13, No. 9, pp. 2367-2370.
U.S. Appl. No. 13/761,530, filed Feb. 7, 2013.

\* cited by examiner

*Primary Examiner* — Ruth Davis
(74) *Attorney, Agent, or Firm* — Craig R. Miles; CR Miles, P.C.

(57) ABSTRACT

An IVF system for successfully utilizing spermatozoa separated into X-chromosome bearing and into Y-chromosome bearing population for insemination. The IVF system includes fertilization medium that can shorten the time from insemination to cleavage and a portable incubator for the transportation of maturing oocytes and inseminated oocytes comprising a straw (19) and an incubation element (20) that can be sealed with a cap (22).

18 Claims, 4 Drawing Sheets

IN-VITRO FERTILIZATION SYSTEMS WITH SPERMATOZOA SEPARATED INTO X-CHROMOSOME AND Y-CHROMOSOME BEARING POPULATIONS

This application is a continuation of U.S. patent application Ser. No. 11/508,133, filed Aug. 21, 2006, which is a continuation of U.S. patent application Ser. No. 10/433,191, filed May 29, 2003, now U.S. Pat. No. 7,094,527, issued Aug. 22, 2006, which is the National Stage of International Patent Cooperation Treaty Patent Application No. PCT/US01/45237, filed Nov. 29, 2001, which claims the benefit of U.S. Provisional Patent Application No. 60/253,785, filed Nov. 29, 2000, and U.S. Provisional Patent Application No. 60/253,787, filed Nov. 29, 2000, each hereby incorporated by reference herein.

I. TECHNICAL FIELD

Devices, compositions, and methods that improve the quality of embryos generated using in-vitro fertilization (IVF) with spermatozoa separated into X-chromosome bearing and Y-chromosome bearing populations.

II. BACKGROUND

An attractive feature of IVF is that many fewer spermatozoa can be required for insemination than for artificial insemination. However, WF using spermatozoa separated into X-chromosome bearing and Y-chromosome bearing populations (separated spermatozoa) can necessitate modifications to conventional IVF techniques. This may be due in part to the pre-capacitation of such spermatozoa.

In most cases, the percentages of oocytes (oocyte, ootid, or ova, or plurality of same as appropriate to the application) fertilized with separated and unseparated spermatozoa are similar, and events during the first cell cycle are timed similarly for separated and unseparated spermatozoa. However, with conventional procedures, blastocyst production with separated spermatozoa can be 70%-90% of controls with spermatozoa that have not been separated. For example, development to blastocysts has been shown to be 17% with bovine oocytes inseminated with separated spermatozoa, compared with >25% which might be expected with IVF using unseparated spermatozoa as described in the journal article entitled "In Vitro Fertilization With Flow-Cytometerically-Sorted Bovine Sperm" Theriogenology 52: 1393-1405 (1999), hereby incorporated by reference.

Several factors may contribute to these results. One factor may be that staining of sperm with Hoechst 33342 appears to cause a decline in motility of spermatozoa. Another factor, may be the physical forces the spermatozoa are subject to during the separation process. As but one example, in flow cytometric separation of spermatozoa, spermatozoa exit the flow cytometer at nearly 100 km/h before impacting on the surface of the collection medium. During transit through the flow cytometer spermatozoa can be subjected to laser light at an intensity of over 100 mW. While the transit time may only be 1-2 μsec, this may affect the spermatozoal DNA, and thus, also effect subsequent embryonic development. The process of separating sperm with flow cytometry can also result in a highly diluted sample, 600,000 spermatozoa/mL or less, and subsequent centrifugation steps are necessary to provide concentrated spermatozoa suitable for insemination.

Another problem with utilizing separated spermatozoa in IVF techniques may be that the facility in which the spermatozoa are separated may be in a different location than where the male mammal from which the spermatozoa are collected is located, which may be different from where the female mammal from which the oocytes are collected is located, which may be a different location from where the in-vitro fertilization is to occur, and which may be a different location from where the female mammal into which the in-vitro cultured embryos are to be transferred. Conventionally, separated sperm may be cryopreserved and transported frozen to the facility at which the IVF techniques are administered. Maturing oocytes are conventionally transported to the facility at which the IVF techniques are administered in portable incubation systems. The maturing oocytes are then inseminated with previously frozen-thawed sperm cells. To avoid cryopreservation of sperm cells or as a convenience to the various facilities involved it may be beneficial to transport maturing oocytes directly to the facility separating the spermatozoa so that separated sperm cells can be added to the oocytes without cryopreservation. However, conventional IVF and in vitro culture of the resulting zygotes typically comprises a separate set of apparatus and procedures making it inconvenient, difficult, or impossible to inseminate and culture oocytes in the same facility in which spermatozoa are separated.

Even though X-chromosome bearing spermatozoa and Y-chromosome bearing spermatozoa have been differentiated by and separated based upon the difference in emitted fluorescence for many years, and even though separated spermatozoa have been used for some time with IVF techniques, and even though there is large commercial market for embryos produced with IVF techniques and separated spermatozoa, the above-mentioned problems have yet to be resolved.

As to the problems with conventional techniques of IVF using separated spermatozoa, and specifically separated spermatozoa, stained spermatozoa, or spermatozoa that are from previously frozen sperm, and with conventional strategies involving the transportation of separated sperm and maturing oocytes, the invention addresses each in a practical manner.

III. DISCLOSURE OF THE INVENTION

Accordingly, one of the broad objects of particular embodiments of the invention can be to provide devices, compositions and methods that provide transportation of inseminated oocytes, promotes cleavage of fertilized oocytes and improves the quality of embryos generated with techniques utilizing spermatozoa separated into X-chromosome bearing and Y-chromosome bearing populations.

Another broad object of particular embodiments of the invention can be to provide devices, compositions, and methods that promote cleavage and improve quality of embryos generated using IVF with spermatozoa that are derived from previously frozen sperm.

Another broad object of particular embodiments of the invention can be to provide devices, compositions, and methods that promote cleavage and improve quality of embryos generated using IVF with spermatozoa that have previously been stained with a DNA binding fluorochrome.

Another broad object of particular embodiments of the invention can be to provide medium for embryonic culturing that can contain non-essential amino acids.

Another broad object of the invention can be to provide apparatus and methods for transporting maturing oocytes and fertilized oocytes for the convenience of the end user(s) or to avoid cryopreservation of the spermatozoa used to fertilize oocytes.

Naturally further objects of the invention are disclosed throughout other areas of specification.

IV. BRIEF DESCRIPTION OF THE DRAWINGS

V. MODE(S) FOR CARRYING OUT THE INVENTION

The invention involves devices, methods, and compositions for the in-vitro insemination and fertilization of oocytes (oocyte, ootid, or ova, or plurality of same as appropriate to the application) and the culture of embryos resulting from such techniques.

Embodiments of the invention can include fresh spermatozoa, or spermatozoa from frozen-thawed sperm of numerous species of mammals. The invention should be understood not to be limited to the species of mammals cited by the specific examples within this patent application. Embodiments of the invention, for example, may include fresh spermatozoa or spermatozoa from frozen-thawed sperm of animals having commercial value for meat or dairy production such as swine, bovids, ovids, equids, buffalo, or the like (naturally the mammals used for meat or dairy production may vary from culture to culture). It may also include fresh spermatozoa or spermatozoa from frozen-thawed sperm from individuals having rare or uncommon attribute(s), such as morphological characteristics including weight, size, or conformation, or other desired characteristics such as speed, agility, intellect, or the like. It may include frozen-thawed sperm from deceased donors, or fresh or frozen-thawed spermatozoa from rare or exotic mammals, such as zoological specimens or endangered species. Embodiments of the invention may also include fresh or frozen-thawed spermatozoa collected from primates, including but not limited to, chimpanzees, gorillas, or the like, and may also include fresh or frozen-thawed spermatozoa from marine mammals, such as whales or porpoises.

Figure 1:
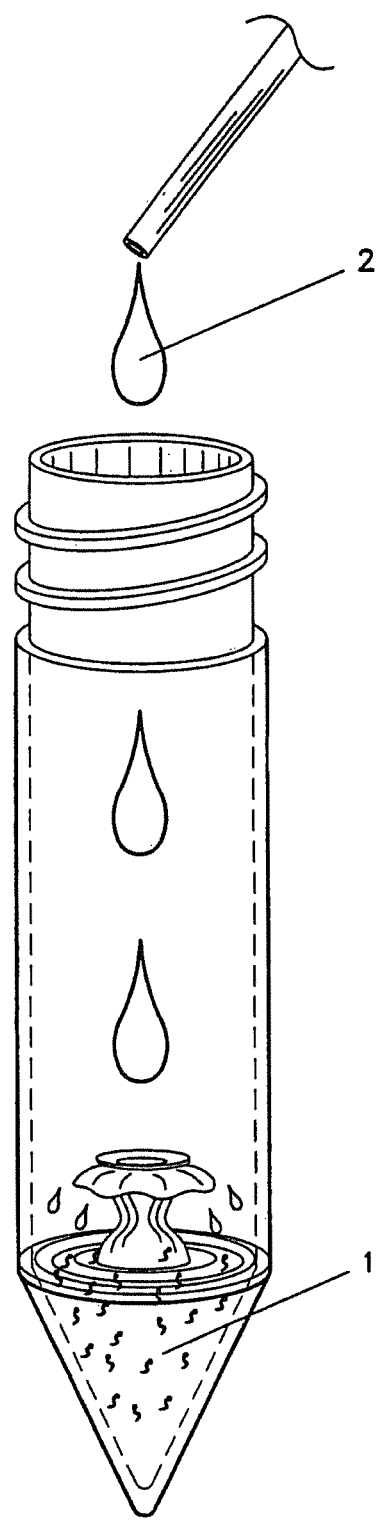
FIG. 1 shows an embodiment of the invention in which spermatozoa from fresh or previously frozen-thawed sperm are stained.

Now referring primarily to FIG. 1, in some embodiments of the invention, Hoechst 33342 stain (1) can be added to bovine spermatozoa contained in frozen-thawed sperm (2) to establish a concentration of 224 µM. The incubation time of the spermatozoa contained in the frozen-thawed sperm (2) with the stain (1) can be about 190 minutes. In anther embodiment of the invention, the stain (1) can be added to the bovine sperm (2) to establish a concentration of 2240 µM and then incubated for about 60 minutes. Frozen-thawed sperm treated in either manner can improve the resolution of X-chromosome bearing from Y-chromosome bearing spermatozoa. Understandably, from application to application (such as frozen-thawed sperm from different species) the amount of incubation time and the specific concentration of stain can be adjusted to optimize the resolution of the X-chromosome bearing from Y-chromosome bearing spermatozoa.

With respect to the cleavage rates of inseminated oocyte(s), the increase in stain concentration up to at least 10× does not appear to have a depressive effect on either cleavage or embryonic development. Higher stain concentrations may actually be beneficial with respect to certain applications because the length of incubation time may be decreased improving percent cleavage. From application to application length of incubation time can be adjusted to optimize cleavage results or embryonic development, as desired.

Figure 2:
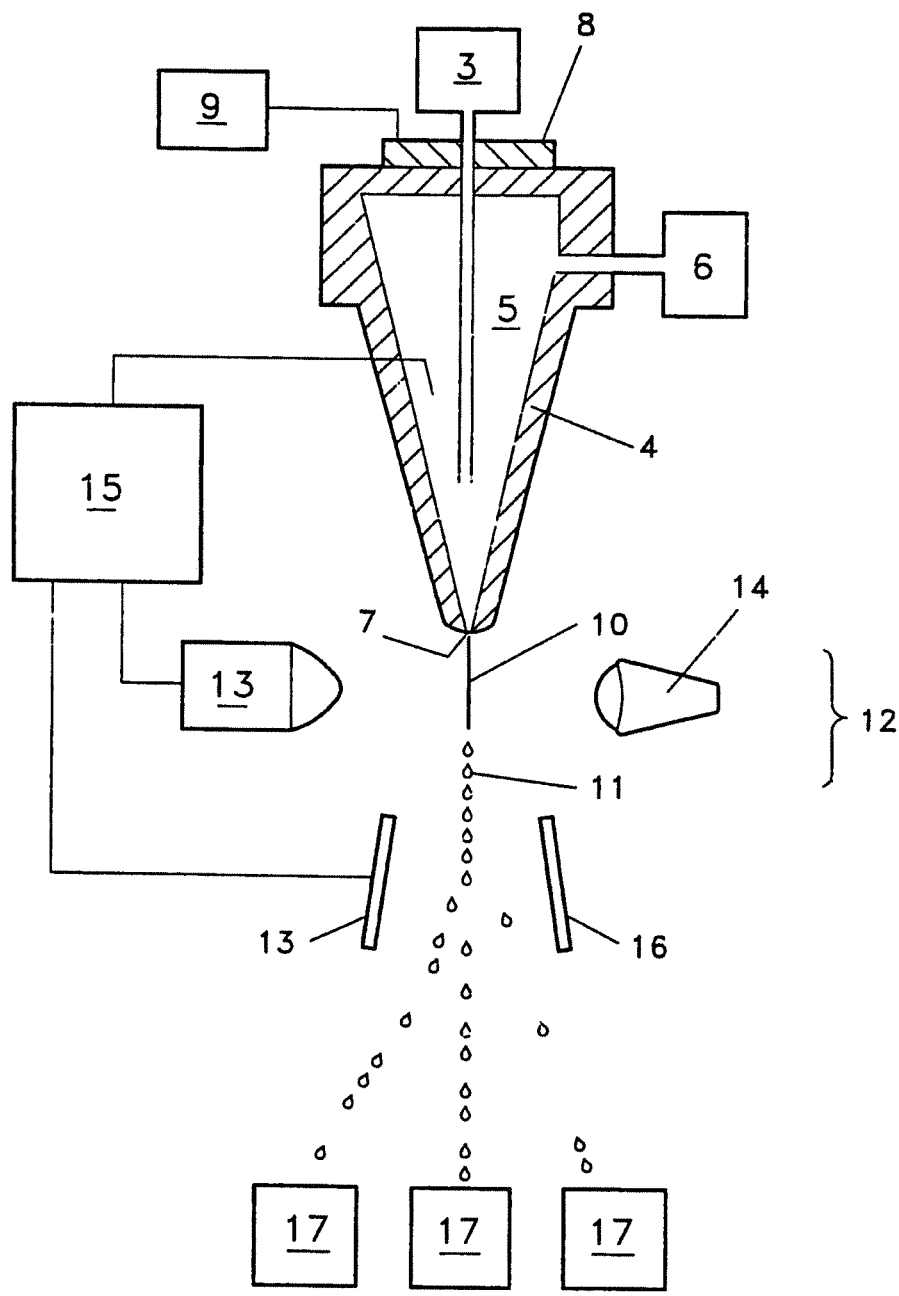
FIG. 2 shows an embodiment of the invention for separating stained spermatozoa in to X-chromosome bearing and Y-chromosome bearing populations.
Figure 3:
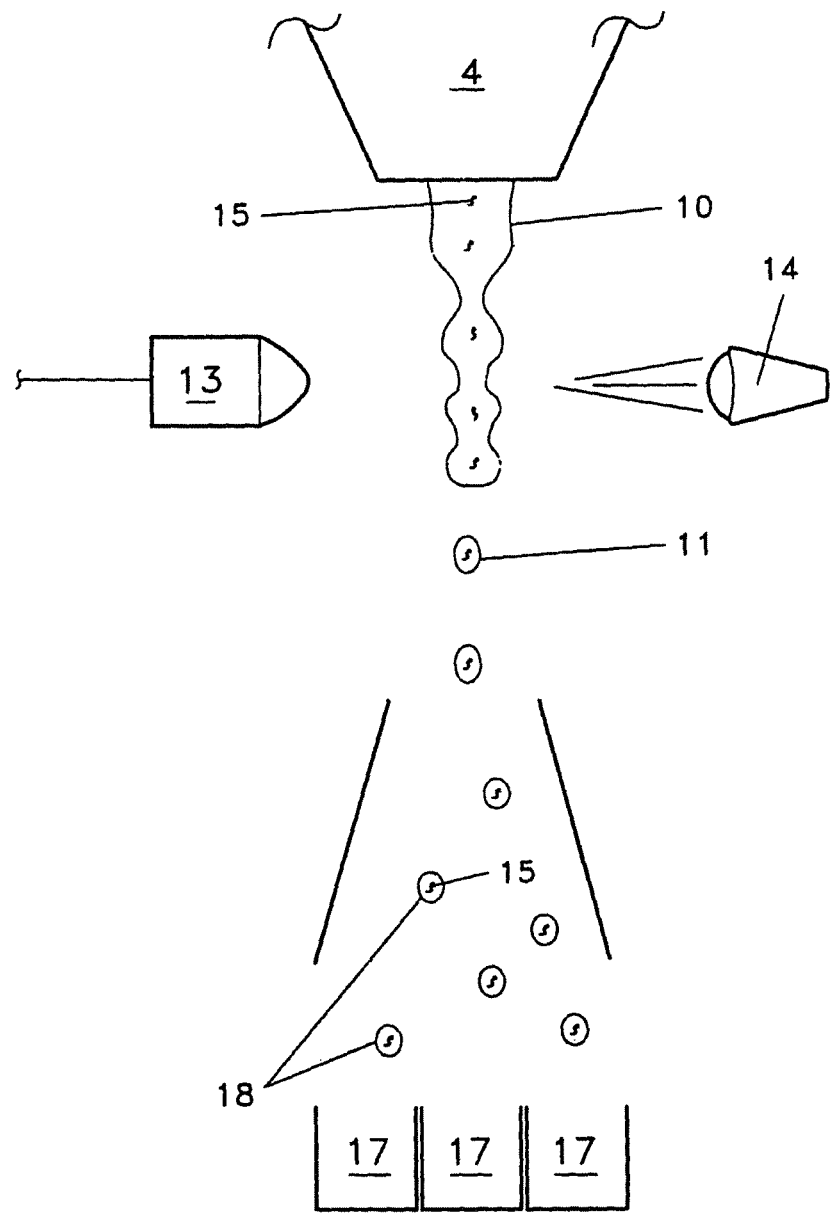
FIG. 3 shows another view of an embodiment of the invention for separating stained spermatozoa in to X-chromosome bearing and Y-chromosome bearing populations.

Now referring primarily to FIGS. 2 and 3, a flow cytometer embodiment of the invention is shown which includes a sperm cell source (3) which acts to establish or supply stained spermatozoa or other type of stained cells to be analyzed by the flow cytometer. The sperm cells are deposited within a nozzle (4) in a manner such that the cells are surrounded by a sheath fluid (5). The sheath fluid (5) is usually supplied by some sheath fluid source (6) so that as the cell source (3) supplies sperm cells, the sheath fluid (5) is concurrently fed through the nozzle (4). In this manner it can be easily understood how the sheath fluid (5) forms a sheath fluid environment for the cells. Since the various fluids are provided to the flow cytometer at some pressure, they flow out of the nozzle (4) and exit at the nozzle orifice (7). By providing some type of oscillator (8) which may be very precisely controlled through an oscillator control (9), pressure waves may be established within the nozzle (4) and transmitted to the fluids exiting the nozzle (4) at nozzle orifice (7). Since the oscillator (9) thus acts upon the sheath fluid (5), the stream (10) exiting the nozzle orifice (7) eventually and regularly forms drops (11). Because the sperm cells are surrounded by a sheath fluid environment, the drops (11) may contain within them individually isolated (generally) cells or other items.

Since the drops (11) generally contain isolated sperm cells, the flow cytometer can distinguish and separate droplets based upon whether or not the appropriate sperm cell is contained within the drop. This is accomplished through a cell sensing system (12). The cell sensing system involves at least some type of sensor (14) which responds to the cells contained within each drop (11) as described by U.S. Pat. No. 5,135,759, hereby incorporated by reference. As the Johnson patent explains for spermatozoa or sperm cells, although the staining and separation inventions can be understood to be used with a variety of frozen-thawed cells, the cell sensing system (12) may cause an action depending upon the relative presence or relative absence of the bound fluorochrome which may be excited by some stimulant such as the laser exciter (13). While each type of sperm cell can be stained by the stain or fluorochrome, as described above, the differing length of the X-chromosome and the Y-chromosome causes different amounts of stain to be bound. Thus, by sensing the degree of fluorescence emitted by the fluorochrome upon excitation it is possible to discriminate between X-bearing spermatozoa and Y-bearing spermatozoa by their differing fluoresence emission levels.

In order to achieve separation and isolation of the appropriate sperm cells, the signals received by sensor (14) are fed to some type of sorter discrimination system (15) which very rapidly makes a differentiation decision and can differentially charge each drop (11) based upon whether it has decided that the desired sperm cell does or does not exist within that drop (11). In this manner the separation or discrimination system (15) acts to permit the electrostatic deflection plates (16) to deflect drops (11) based on whether or not they contain the appropriate sperm cell. As a result, the flow cytometer acts to sort the sperm cells by causing them to land in one or more collectors (17). Thus by sensing some property of the sperm cells the flow cytometer can discriminate between sperm cells based on a particular characteristic and place them in the appropriate collector (17). In the system presently used to sort spermatozoa, the X-bearing spermatozoa droplets are charged positively and thus deflect in one direction, the Y-bearing spermatozoa droplets are charged negatively and thus deflect the other way, and the wasted stream (that is unsortable cells) is uncharged and thus is collected in an undeflected stream into a suction tube or the like.

Now referring primarily to FIG. 3, the process can be even further understood. As shown in that figure, the nozzle (4) emits a stream (10) which because of the oscillator (8) (not shown in FIG. 3) forms drops (11). Since the cell source (3) (not shown in FIG. 3) may supply sperm cells (1) which have been stained according the invention, the magnitude of the fluorescent emission stimulated by the laser exciter (13) is differentially determined by sensor (14) so that the existence or nonexistence of a charge on each drop (11) as it separates from stream (10) can be controlled by the flow cytometer. This control results in positively charged, negatively charged, and uncharged drops based upon the encapsulated sperm cell. As shown in FIG. 3, certain drops are shown as deflected drops (18). These deflected drops (18) are those containing sperm cells (2) differentiated by bearing an X-chromosome or a Y-chromosome. Separated sperm are then deposited in the appropriate collector (17) for later use. See also, International Patent Application PCT/US98/27909, hereby incorporated by reference.

While the above description focuses on the separation of spermatozoa with flow cytometry, separation of X-chromosome bearing spermatozoa and Y-chromosome bearing spermatozoa based upon the difference in measurable fluorescent emission may also include numerous other technologies such as liquid chromatography, gel electrophoresis, and other technologies that similarly excite the amount of bound fluorochrome to differentiate between X chromosome bearing spermatozoa and the Y chromosome bearing spermatozoa.

Embodiments of the invention can also comprise collecting oocytes from a female mammal. With respect to certain embodiments of the invention, oocytes can be aspirated from the ovaries of the desired female mammal or can be obtained from slaughterhouse ovaries. The oocytes can be matured in TCM199 supplemented with about 10% fetal calf serum plus hormones (15 ng FSH, 1 μg LH, 1 μg $E_2$/ml) for 22-24 h at 39° C., in about 5% $CO_2$ in air.

Ten to 15 oocytes can be transferred to a 50 μl drop of fertilization medium containing non-essential amino acids, such as tyrode albumin lactaate pyruvate (TALP) supplemented with non-essential amino acids derived from Eagles Medium, and which can further contain 0.6% bovine serum albumin, 20 μg heparin/mL and 5 mM caffeine. Alternately, oocytes can be fertilized in other medium containing non-essential amino acids such as the chemically defined medium described in the journal article entitled "Lowered Oxygen Tension and EDTA Improve Bovine Zygote Development In Chemically Defined Medium", J. Anim. Sci. (1999), or the SOF medium described in the journal article "Successful Culture In-vitro of Sheep and Cattle Ova", J. Reprod. Fertil. 30:493-497 (1972), each journal article hereby incorporated by reference.

After separating or sorting, sperm cells can be washed by centrifugation for about 10 min at 400 g in collection medium (typically Hepes-tyrode albumin lactate pyruvate medium supplemented with 2.0% bovine serum albumin) followed by suspension in the fertilization medium. Thawed, sorted sperm can be prepared by being centrifuged for 20 minutes at 700 g through a Percoll gradient (90%: 45%) for separation of live and dead sperm. The sperm pellet can then be washed with fertilization medium by centrifugation at 400 g for 10 minutes. Sperm can then be added to the fertilization medium to give a concentration of 1-2 million/mL.

TABLE 1

Cleavage Stage of Oocytes Inseminated with Separated Sperm in Four Different Fertilization Media.

| Media | No. oocytes | % cleavage | % 2-cell at 24 h | % 8-cell at 72 h |
|---|---|---|---|---|
| Fert-TALP | 168 | 76 | 6[a] | 66 |
| Fert-TALP + neaa | 176 | 71 | 26[b] | 67 |
| CDM | 167 | 89 | 75[c] | 70 |
| SOF | 145 | 86 | 49[d] | 69 |

[a,b,c,d]Means with different superscripts differ (P < .05).

Now referring primarily to Table 1, as can be understood, oocytes inseminated with separated spermatozoa in fertilization medium containing non-essential amino acids according to the invention exhibit an increased rate of early development through at least the two cell stage.

TABLE 2

Embryonic Development and Blastocyst Quality Resulting From Fertilization in Four Different Fertilization Media (averaged over two culture media)

| Media | No. oocytes | % blastocysts/oocyte | | % Grade 1 blastocysts/total blastocysts |
|---|---|---|---|---|
| | | Total | D7 | |
| Fert-TALP | 326 | 20 | 17 | 52[a,c] |
| Fert-TALP-aa | 221 | 20 | 17 | 68[b] |
| CDM | 332 | 22 | 18 | 61[b,c] |
| SOF | 321 | 21 | 17 | 64[b,c] |

[a,b,c]Percentages without common superscripts differ (P < .05)
[d]Grade 1 indicates blastocysts with a distinct inner cell mass suitable for embryo transfer.

Now referring primarily to Table 2, some embodiments of the invention in which oocytes are fertilized with sorted spermatozoa in fertilization medium containing supplemented non-essential amino acids can exhibit an enhanced quality of embryos. In embodiments of the invention in which oocytes were fertilized in tyrode albumin lactaate pyruvate (TALP) supplemented with non-essential amino acids derived from Eagles Medium, and further containing 0.6% bovine serum albumin, 20 μg heparin/mL and 5 mM caffeine there was a difference (P<0.05) in quality of embryos as compared to TALP without non-essential amino acids.

Presumptive zygotes can be removed from culture and placed in chemically-defined medium (CDM-1) as discussed in the *Journal Animal Science*, 78, 152-157 (2000), hereby incorporated by reference, for 6-7 hours after insemination and cultured for 65-66 hours. Embryos that cleaved were further cultured 96 hours in CDM-2 (further containing MEM essential and non-essential amino acids and 2.0 mM fructose) containing 0.12 IU insulin/mL. Blastocysts were morphologically graded according to the size of inner cell mass and stained with Giemsa to determine cell numbers on day 7 after insemination.

Figure 4:
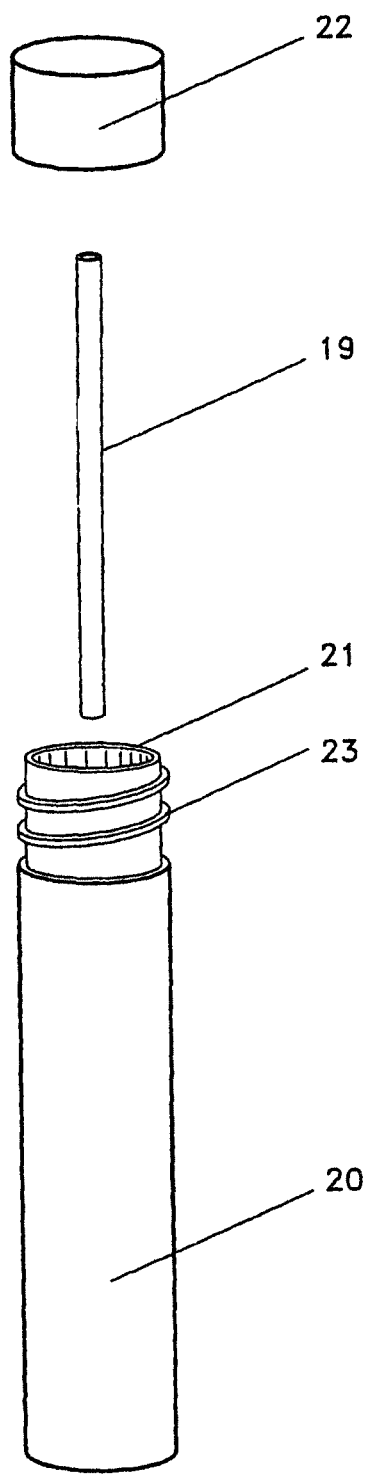
FIG. 4 shows an embodiment of a portable incubation system in which oocytes can be fertilized.

Now referring primarily to FIG. 4, the invention further involves a portable incubation system. Certain embodiments of the invention can comprise a straw (19) having an interior volume between about 0.1 mL and about 0.5 mL into which fertilization medium, and oocytes collected from a female mammal, can be transferred. While the straw (19) could be made of any material compatible with the fertilization medium and the collected oocytes, specific embodiments of the straw (19) can be made of plastic, such as or similar to an artificial insemination straw. The ends of plastic straws can be heat sealed after the fertilization medium and the oocytes are transferred inside.

The invention can further comprise an incubation element (20) configured to encapsulate the straw (19) or a plurality of straws inserted within. In some embodiments of the invention the incubation element (20) can be a glass tube having a single sealable aperture element. The aperture element (21) can be sealed with a cap (22), and in some embodiments the cap (22) and the tube can have spiral threads (23) that can be rotationally mated to close the incubation element (20).

After transfer of a straw (19) or a plurality of straws to the interior volume of the incubation element (20), incubation conditions can be established within. Typical incubation conditions within the interior volume of the incubation element can comprise an atmosphere of five percent carbon dioxide in air and a temperature of about 39° C. (37° C. to 41° C.). Once incubation conditions are established within the incubation element, the incubation element (20) can be sealed and the oocytes can then be transported within the incubation element (20).

In some embodiments of the invention, oocytes can be transported to a sperm cell separation facility where the incubation element (20) is unsealed, the straw (19) is unsealed and a plurality of sperm cells (15) from a population separated on the basis of bearing an X-chromosome or bearing a Y-chromosome can be transferred into the straw (19) containing the oocytes. With respect to some embodiments of the invention a concentration of separated sperm cells (15) can be established of between about 1 million to about 2 million/mL of the fertilization medium. The straw (19) containing the oocytes and spermatozoa in fertilization medium can then be resealed and transferred back into the incubation element (20). The incubation conditions can be re-established and the incubation element sealed. The incubation element (20) containing a straw or plurality of straws (19) can then be transported. During transport the oocytes can become fertilized. Upon arrival zygotes can be transferred from the straw for further culture.

With respect to certain embodiments of the invention, oocytes can first be inseminated with separated or unseparated spermatozoa in conventional 50 μl drops and loaded into a 0.25 mL straw or straws (19) within two hours after insemination. Straws (19) can be heat sealed and put into the incubation element (20). The open incubation element containing straws with inseminated oocytes can be equilabrated with 5% carbon dioxide in air at about 39° C. for at least one hour and then tightly capped and cultured under the same conditions for between about 18-20 hours.

Again referring primarily to Table 2, fewer oocytes ($P<0.05$) fertilized in Fert-TALP developed to the 2-cell stage by 24 hours than in any other media. Notably, the vast majority of oocytes (75%) fertilized in CDM medium cleaved to 2-cell stabe by this time. By 72 hours post-insemination, there was no difference between any of the media, possibly due to the long 8-cell stage cell cycle.

There was no difference between any of the media on rate of development to blastocysts. However, there was a significant difference in quality of embryos between Fert-TALP and Fert-TALP+non-essential amino acids.

Progression of early bovine embryonic development using separated sperm are similar to studies with in-vivo or in-vitro cleavage of oocytes fertilized with unseparated spermatozoa. In the cow the first in-vivo cleavage occurs at 24-28 hours following ovulation, and the first in-vitro cleavage tages place at 24-48 hours after insemination.

Earlier cleavage occurred with oocytes fertilized in CDM, SOF, and Fert-TALP+aa medium than in conventional Fert-TALP medium. This can be because CDM, SOF, and Fert-TALP+non-essential amino acids, all contain non-essential amino acids, which may play a role in how quickly spermatozoa penetrate oocytes, of in the length of the first cell cycle.

As can be easily understood from the foregoing, the basic concepts of the present invention may be embodied in a variety of ways. It involves the staining of spermatozoa, whether fresh spermatozoa or frozen-thawed spermatozoa, separation and isolation techniques which may be used with such stained spermatozoa, as well as devices to accomplish the staining, separation, isolation of such stained spermatozoa into X-chromosome bearing and Y-chromosome bearing populations, and the transporting of maturing oocytes and fertilized oocytes. In this patent application, the staining and separating techniques used with spermatozoa are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this patent application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function is accomplished by a device, subroutine, or program. Apparatus claims may not only be included for the devices described, but also method or process claims may be included to address the functions the invention and each element performs. Neither the description nor the terminology is intended to limit the scope of the claims which now be included.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sorter" should be understood to encompass disclosure of the act of "sorting"—whether explicitly discussed or not—and, conversely, were there only disclosure of the act of "sorting", such a disclosure should be understood to encompass disclosure of a "sorter" and even a "means for sorting".

Such changes and alternative terms are to be understood to be explicitly included in the description.

Additionally, the various combinations and permutations of all elements or applications can be created and presented. All can be done to optimize the design or performance in a specific application.

Any acts of law, statutes, regulations, or rules mentioned in this application for patent: or patents, publications, or other references mentioned in this application or any parent application for patent are hereby incorporated by reference. Specifically, U.S. application Ser. No. 10/433,191, filed May 29, 2003, International Application No. PCT/US01/45237, filed Nov. 29, 2001, U.S. Provisional Patent Application No. 60/253,787, filed Nov. 29, 2000 and U.S. Provisional Patent Application No. 60/253,785, filed Nov. 29, 2000, are hereby incorporated by reference including any figures or attachments.

In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in an Information Disclosure Statement or other information statement filed with this application or in any parent applications are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

Thus, the applicant(s) should be understood to have support to claim at least: i) each of the staining, separation, isolation, insemination, or fertilization procedures as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and x) the various combinations and permutations of each of the elements disclosed.

The claims set forth in this specification or in a parent specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the subject matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of in-vitro fertilization of oocytes, comprising:
    a) obtaining oocytes of a non-human mammal;
    b) obtaining stained sperm cells of said non-human mammal, said stained sperm cells separated by a flow cytometer into an X-chromosome bearing population or a Y-chromosome bearing population;
    c) combining said oocytes in a fertilization medium with said stained sperm cells separated by said flow cytometer, said stained sperm cells of either one of said X-chromosome bearing population or said Y-chromosome bearing population; and
    d) fertilizing in-vitro at least one of said oocytes with said stained sperm cells of either one said X-chromosome bearing population or said Y-chromosome bearing population to produce sex-selected embryos capable of blastocyst formation.

2. The method of in-vitro fertilization of oocytes of claim 1, wherein said fertilization medium contains an amount of non-essential amino acids.

3. The method of in-vitro fertilization of oocytes of claim 2, further comprising sufficiently supplementing said fertilization medium with said non-essential amino acids to achieve an increased rate of development through at least a two cell stage.

4. The method of in-vitro fertilization of oocytes of claim 3, wherein said non-human mammal is a bovine non-human mammal, and wherein said step of achieving said increased rate of development through at least said two cell stage is selected from the group consisting of:
    achieving at least about a 20% increase in yield of said two cell stage;
    achieving at least about a 45% increase in yield of said two cell stage;
    achieving at least about a 70% increase in yield of said two cell stage;
    achieving at least about a 26% yield of said two cell stage;
    achieving at least about a 49% yield of said two cell stage; and
    achieving at least about a 75% yield of said two cell stage.

5. The method of in-vitro fertilization of oocytes of claim 2, wherein said oocytes fertilized with said stained sperm cells of said X-chromosome bearing population or said Y-chromosome bearing population in said fertilization medium containing said non-essential amino acids achieve an increased rate of said sex-selected blastocysts suitable for embryo transfer.

6. The method of in-vitro fertilization of oocytes of claim 5, wherein said non-human mammal is a bovine non-human mammal, and wherein said step of achieving said increased rate of said sex-selected blastocysts suitable for embryo transfer is selected from the group consisting of:
    achieving at least about a 9% increase in said rate of blastocysts;

achieving at least about a 12% increase in said rate of blastocysts;
achieving at least about a 16% increase in said rate of blastocysts;
achieving at least about a 52% yield of said blastocysts;
achieving at least about a 61% yield of said blastocysts;
achieving at least about a 64% yield of said blastocysts; and
achieving at least about a 68% yield of said blastocysts.

7. The method of in-vitro fertilization of oocytes of claim 5, wherein said non-human mammal comprises a bovine non-human mammal, and wherein said sex-selected blastocysts comprise Grade 1 blastocysts.

8. The method of in-vitro fertilization of oocytes of claim 1, further comprising supplementing said fertilization medium with an amount of non-essential amino acids.

9. The method of in-vitro fertilization of oocytes of claim 1, wherein said stained sperm cells comprise frozen-thawed stained sperm cells of said non-human mammal prior separated by said flow cytometer into said X-chromosome bearing population or said Y-chromosome hearing population.

10. The method in-vitro fertilization of bovine oocytes as described in claim 1, further comprising establishing said plurality of oocytes with said stained sperm cells of said X-chromosome bearing population or said Y-chromosome bearing population in incubation conditions within an incubation element.

11. The method of in-vitro fertilization of oocytes of claim 10, wherein said incubation conditions comprise an atmosphere of about 5 percent carbon dioxide in air at a temperature between about 37 degrees Centigrade and about 41 degrees Centigrade for a duration of about 18 hours to about 20 hours.

12. The method of in-vitro fertilization of oocytes of claim 11, further comprising transferring said oocytes and said stained sperm cells into a tubular member.

13. The method of in-vitro fertilization of oocytes of claim 12, wherein said tubular member has heat sealable aperture elements.

14. The method of in-vitro fertilization of oocytes of claim 13, wherein said tubular member has an interior volume of about 0.25 milliliters.

15. The method of in-vitro fertilization of oocytes of claim 12, further comprising transferring said tubular member into an incubation element.

16. The method of in-vitro fertilization of oocytes of claim 15, wherein said incubation element comprises a glass tube.

17. The method of in-vitro fertilization of oocytes of claim 16, wherein said tubular member comprises an artificial insemination straw.

18. The method of in-vitro fertilization of oocytes of claim 1, wherein said first and second non-human mammal is selected from the group consisting of non-human primates, bovids, ovids, equids, swine, and dolphins.

\* \* \* \* \*